United States Patent
Ponsi et al.

(10) Patent No.: US 8,152,749 B2
(45) Date of Patent: Apr. 10, 2012

(54) STABILIZATION WEDGE FOR ULCER PREVENTION AND THERAPEUTIC/TREATMENT BOOT

(75) Inventors: Lawrence G. Ponsi, Wheeling, IL (US); James P. Layer, Crystal Lake, IL (US)

(73) Assignee: Sage Products, Inc., Cary, IL (US)

( * ) Notice: Subject to any disclaimer, the term of this patent is extended or adjusted under 35 U.S.C. 154(b) by 495 days.

(21) Appl. No.: 12/389,185

(22) Filed: Feb. 19, 2009

(65) Prior Publication Data

US 2009/0149791 A1   Jun. 11, 2009

Related U.S. Application Data

(63) Continuation-in-part of application No. 11/855,560, filed on Sep. 14, 2007.

(51) Int. Cl.
*A61F 5/00* (2006.01)
*A61F 13/00* (2006.01)

(52) U.S. Cl. ............... 602/65; 602/27; 602/60; 602/62; 128/882

(58) Field of Classification Search ............... 602/60–65, 602/23, 27; 5/649–651, 648; 36/88–90; 128/882, 878, 879; D24/190–192; D6/601
See application file for complete search history.

(56) References Cited

U.S. PATENT DOCUMENTS

| | | | | |
|---|---|---|---|---|
| 3,903,878 A | * | 9/1975 | Spann | 602/21 |
| 3,913,243 A | * | 10/1975 | Arnold et al. | 36/135 |
| 4,135,504 A | * | 1/1979 | Spann | 602/24 |
| 4,924,605 A | * | 5/1990 | Spademan | 36/114 |
| 5,046,487 A | * | 9/1991 | Scott | 601/27 |
| 5,832,632 A | * | 11/1998 | Bergeron | 36/58.5 |
| 5,921,949 A | * | 7/1999 | Dray | 602/64 |
| 6,120,472 A | * | 9/2000 | Singer, Jr. | 602/64 |
| 6,182,311 B1 | * | 2/2001 | Buchanan et al. | 5/632 |
| 6,585,674 B2 | * | 7/2003 | Toda | 602/62 |
| D523,679 S | * | 6/2006 | Illingworth | D6/601 |
| 2009/0084390 A1 | * | 4/2009 | Davis et al. | 128/882 |

* cited by examiner

*Primary Examiner* — Kim M Lewis
(74) *Attorney, Agent, or Firm* — Brinks Hofer Gilson & Lione (57) ABSTRACT

A device for stabilizing a limb, typically when the limb is in a prevention and therapeutic/treatment boot. A wedge-shaped stabilization block includes an outwardly-extending tether. In one form of the invention, a fastener in the form of spaced fastener elements is located on the tether for securing the stabilization block in place. In a second form of the invention, the stabilization block is permanently affixed to the boot and may include fastener elements for engaging complementary fastener elements on the boot.

17 Claims, 7 Drawing Sheets

STABILIZATION WEDGE FOR ULCER PREVENTION AND THERAPEUTIC/TREATMENT BOOT

RELATED APPLICATION

This application is a continuation-in-part of co-pending U.S. patent application Ser. No. 11/855,560, filed Sep. 14, 2007.

BACKGROUND OF THE INVENTION

This invention relates to stabilization of a limb in a patient setting, and in particular to a device for use as an adjunct for limb stabilization.

In co-pending U.S. patent application Ser. No. 11/240,679 filed Sep. 30, 2005 and assigned to the assignee of the present application, a heel ulcer prevention and cushioning boot is disclosed and described. The boot provides heel elevation, support and comfort, as well as proper positioning of a patient's leg to avoid creating other problems, such as ulcers.

Sometimes, for whatever reasons, including inability of the patient to maintain proper orientation of a limb, the heel ulcer prevention and cushioning boot may need additional stabilization to maintain the proper limb orientation. The present invention provides that additional stabilization

SUMMARY OF THE INVENTION

The invention is directed to a stabilized prevention and therapeutic/treatment boot comprising a boot shaped to engage a foot and lower leg, a stabilization block, and a tether secured to and extending from the block and secured to and extending from the boot. A fastener may be provided for temporarily affixing the stabilization block in place on the boot.

In accordance with the preferred form of the invention, the stabilization block is elongated and generally triangular in cross-section. The tether comprises an elongated strap. The fastener comprises a first fastener element on the stabilization block and a second fastener element on the boot. Preferably, the fastener elements comprise hook-and-loop elements.

Preferably, the first fastener element comprises one fastener segment on one face of the stabilization block and a second fastener segment on a second face of the stabilization block. The tether is secured to the block between the faces. Also, preferably, the second fastener element comprises one fastener segment on one side of the boot and a second fastener segment on the opposite side of the boot, with the tether being secured to the boot between the fastener segments on the boot.

In accordance with the method of the invention, as described above, the therapeutic boot includes at least one fastener segment on the boot, and the method comprises tethering the stabilization block to the boot at a fixation location proximate the fastener segment with a strap of a length at least sufficient to extend from the fixation location to the fastener segment. Then, the stabilization block is pivoted about the strap to engage a fastener segment on the stabilization block with a fastener segment on the boot. Preferably, the tethering of the stabilization block to the boot at the fixation location is at a point approximately equidistance between the first and second fastener segments on opposite sides of the boot.

BRIEF DESCRIPTION OF THE DRAWINGS

The invention is described in greater detail in the following description of examples embodying the best mode of the invention, taken in conjunction with the drawing figures, in which.

DESCRIPTION OF EXAMPLES EMBODYING THE BEST MODE OF THE INVENTION

Figure 1:
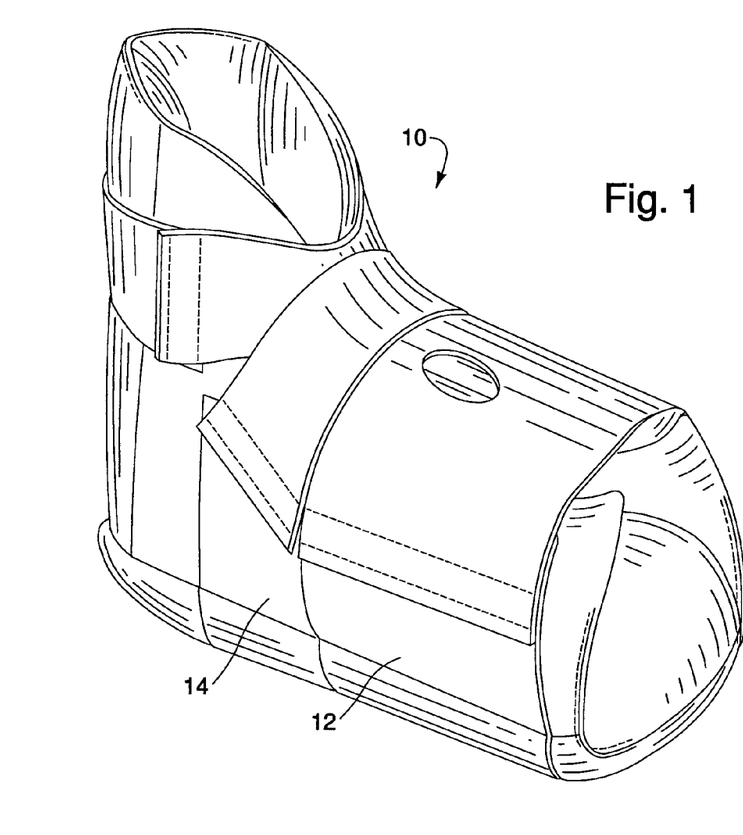
FIG. 1 is a perspective view of a prevention and therapeutic/treatment boot for which the invention of the present application is particularly suitable.

The stabilization wedge according to the invention is particularly suitable for use in combination with a prevention and therapeutic/treatment boot, such as the boot 10 illustrated in FIG. 1. The boot 10 is described in greater detail in co-pending U.S. patent application Ser. No. 11/240,679, filed Sep. 30, 2005, the disclosure of which is incorporated herein by reference. Greater detail can be obtained from that application. Of the many features of the boot 10, hook-and-loop fastener segments 12 and 14 are particularly useful in combination with the stabilization wedge of the present invention, as will become evident from the description below. While the boot 10 is a preferred form of boot to be stabilized, other boots can be employed, as well.

Figure 2:
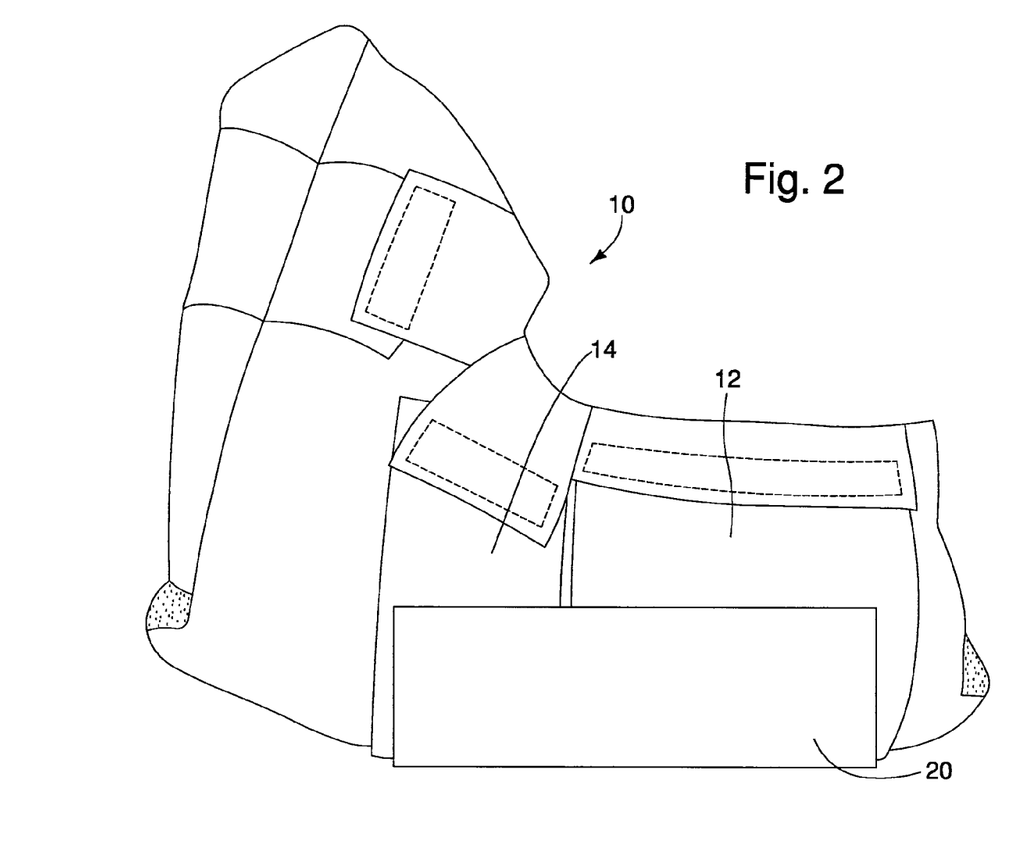
FIG. 2 is an elevational view of the boot of FIG. 1, having the stabilization wedge of the invention in place.
Figure 3:
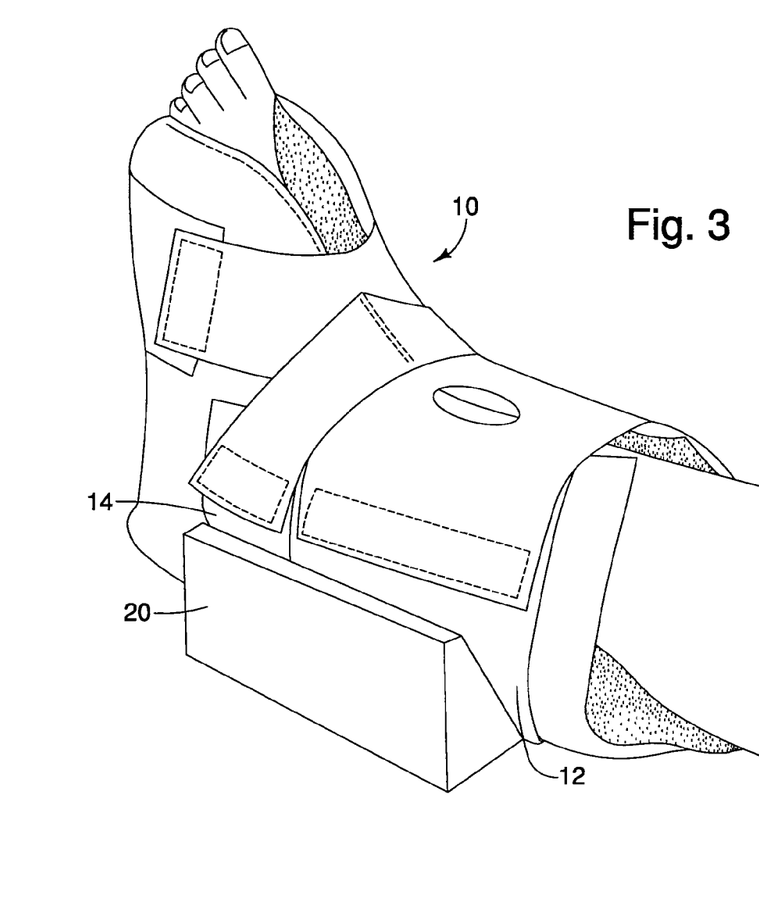
FIG. 3 is a perspective view similar to FIG. 1, with the stabilization wedge in place and showing how a patient's leg is supported.
Figure 4:
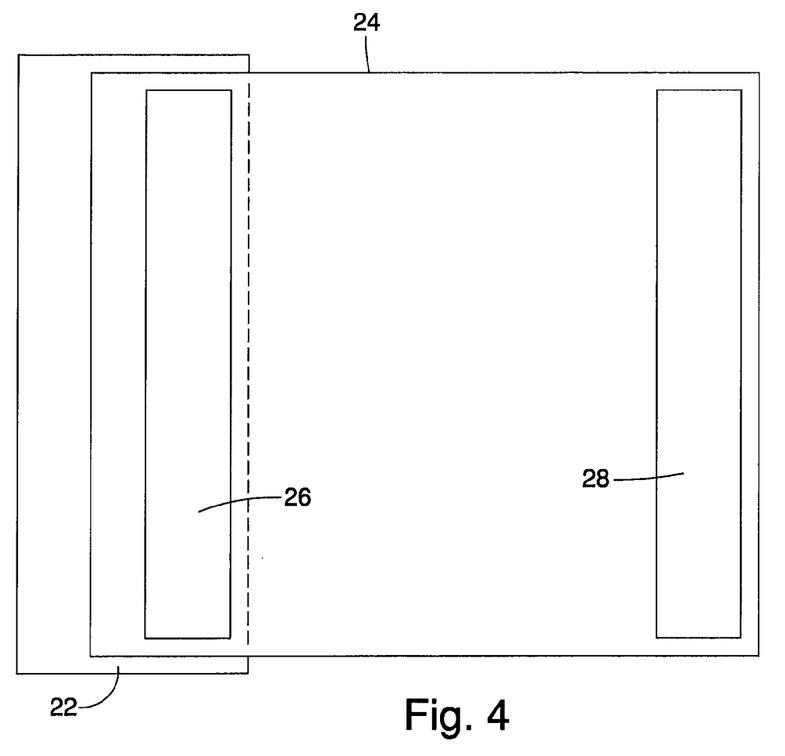
FIG. 4 is a top plan view of the stabilization wedge.
Figure 5:
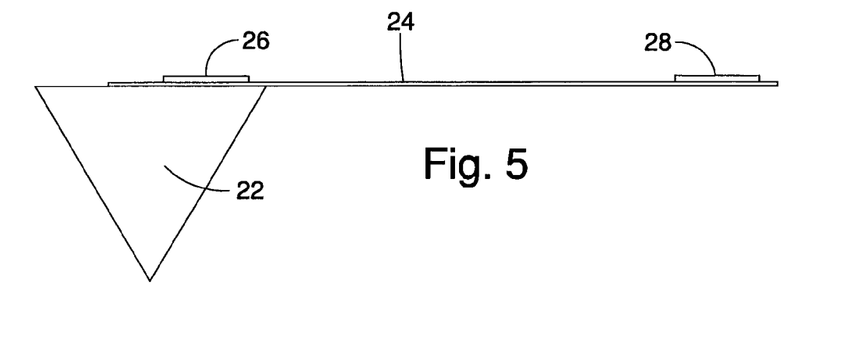
FIG. 5 is an elevational view of the wedge of FIG. 4.

The stabilization wedge of one form of the invention is shown in FIGS. 2 and 3, with a slightly different form shown in FIGS. 4 and 5. The wedge 20 shown in FIGS. 2 and 3 differs from the wedge 22 shown in FIGS. 4 and 5 only in the particular cross-sectional configuration. As shown in FIG. 3, the wedge 20 is generally trapezoidal in cross-section, while the wedge 22 shown in FIGS. 4 and 5 is generally triangular in cross section. Other shapes of the wedges 20 and 22 will be apparent to one skilled in the art, and the invention is not limited to simply a trapezoidal or triangular cross-section.

No matter the cross-section of the wedge 20 or 22, the wedge comprises a stabilization block, and has a tether secured to and extending from the stabilization block. The tether preferably comprises an elongated strap 24, and may be secured to the respective wedge 20 or 22 by any means, such as sonic welding, adhesives, or any other means of forming a permanent connection between the wedge 20 or 22 and the elongated strap 24. The strap 24 is preferably quite flexible, and can be made of any suitable material, such as plastic or fabric. The wedge 20 or 22, on the other hand, is significantly robust to orient the boot 10, and can be formed of any suitable material, such as high density foam, plastic or the like, which has sufficient body to properly orient the boot 10 in its desired position.

As shown in the drawing figures, the wedges 20 and 22 are elongated and for fastening to the boot 10, a fastener is provided in the form of a pair of spaced fastener elements 26 and 28 on the strap 24. The fastener elements 26 and 28 complement the fastener segments 12 and 14, thus one of the segments 12 and 14 or elements 26 and 28 is preferably a hook element, while the other of the fastener segments 12 and 14 and fastener elements 26 and 28 is a loop element. Thus, when the wedge 20 or 22 is applied to the boot 10 as illustrated in the drawing figures, the hook and loop elements engage and hold the wedge 20 or 22 in place.

As illustrated, the fastener elements 26 and 28 are located substantially at opposite ends of the strap 24. The spacing of the fastener elements 26 and 28 is such to advantageously engage the fastener segments 12 and 14. As illustrated, the fastener element 26 is located proximate the stabilization wedge 20 or 22, and the fastener element 28 is located on the elongated strap 24 opposite the fastener element 26.

While the fastener elements 26 and 28 are preferably hook-and-loop fastener segments to advantageously engage the hook-and-loop fastener segments 12 and 14, other types of fastener elements can be employed, as will be evident to one skilled in the art. Permanent fasteners, such as adhesives, can be utilized, as well as other types of temporary connection to the boot, such as various kinds of fasteners or adhesive strips or adhesive elements. The type of connection will be dictated by whether the user wishes a more permanent type of connection, or a readily removable type of connection.

As is evident, the stabilization wedge 20 or 22 can be used on either side of the boot 10. If need be, the wedges 20 or 22 can be doubled, that is, instead of a single wedge proximate the fastener element 26, there can be a second wedge proximate the fastener element 28. Thus, both sides of the boot 10 can be stabilized if needed.

The shape of the wedge 20 or 22 can vary depending upon the nature of the boot 10 and the use in connection with the boot. While two types of wedges 20 and 22 have been illustrated and described, it will be evident that other shapes will perform the stabilization functions as explained, and the element 20 or 22 can be just about any shape, including round in cross section, and still have the desired function.

Figure 6:
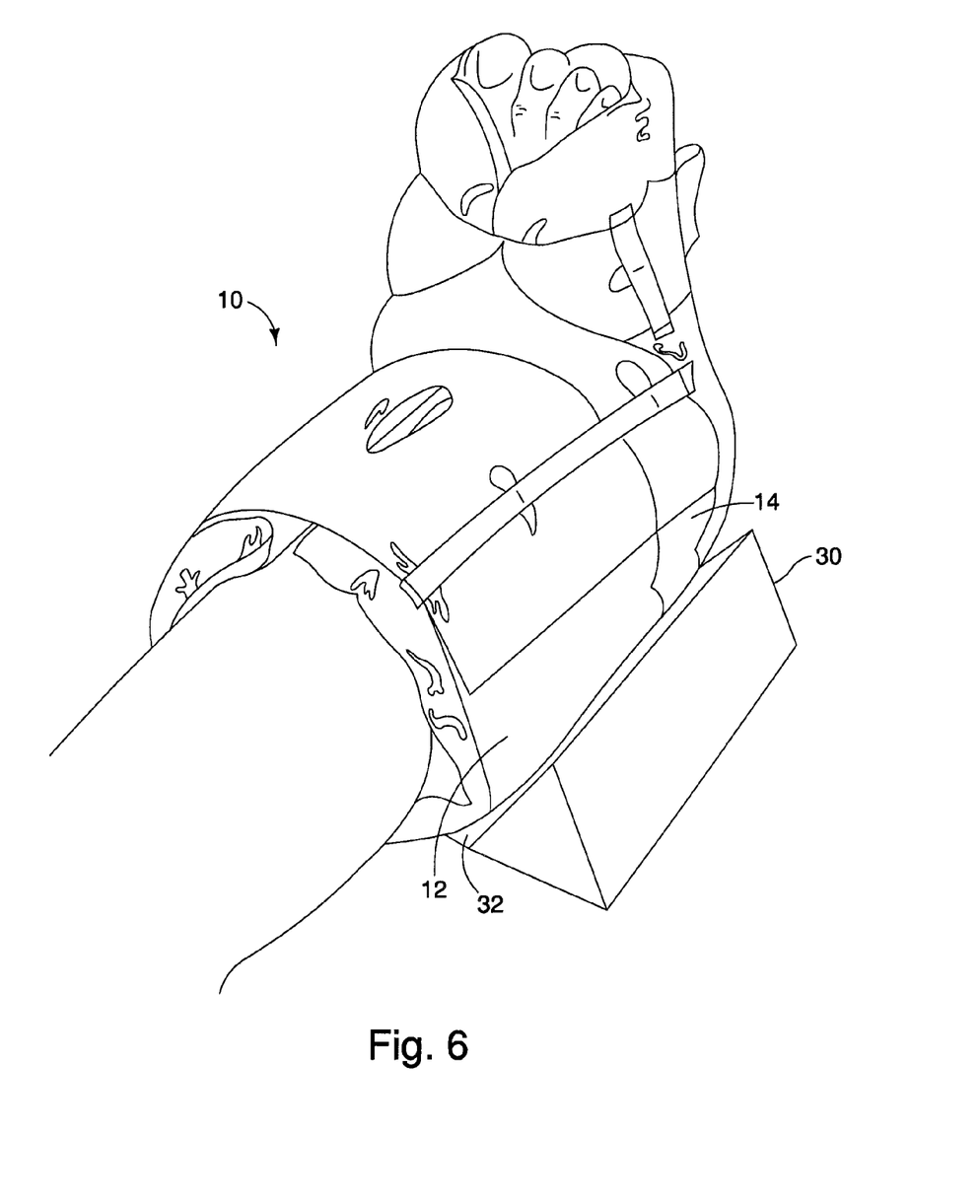
FIG. 6 is a perspective view of a second form of the invention with the stabilization block temporarily affixed to the boot.
Figure 7:
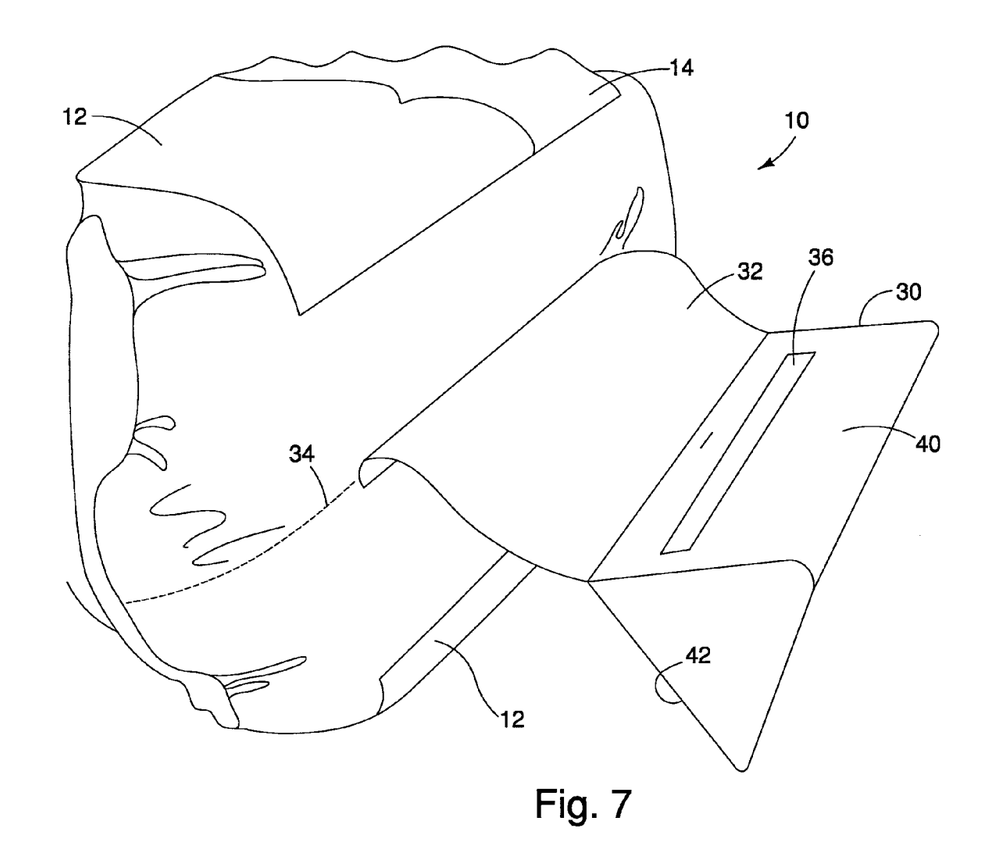
FIG. 7 is a partial bottom perspective view of the form of the invention shown in FIG. 6, illustrating how the stabilization block is tethered to the boot.
Figure 8:
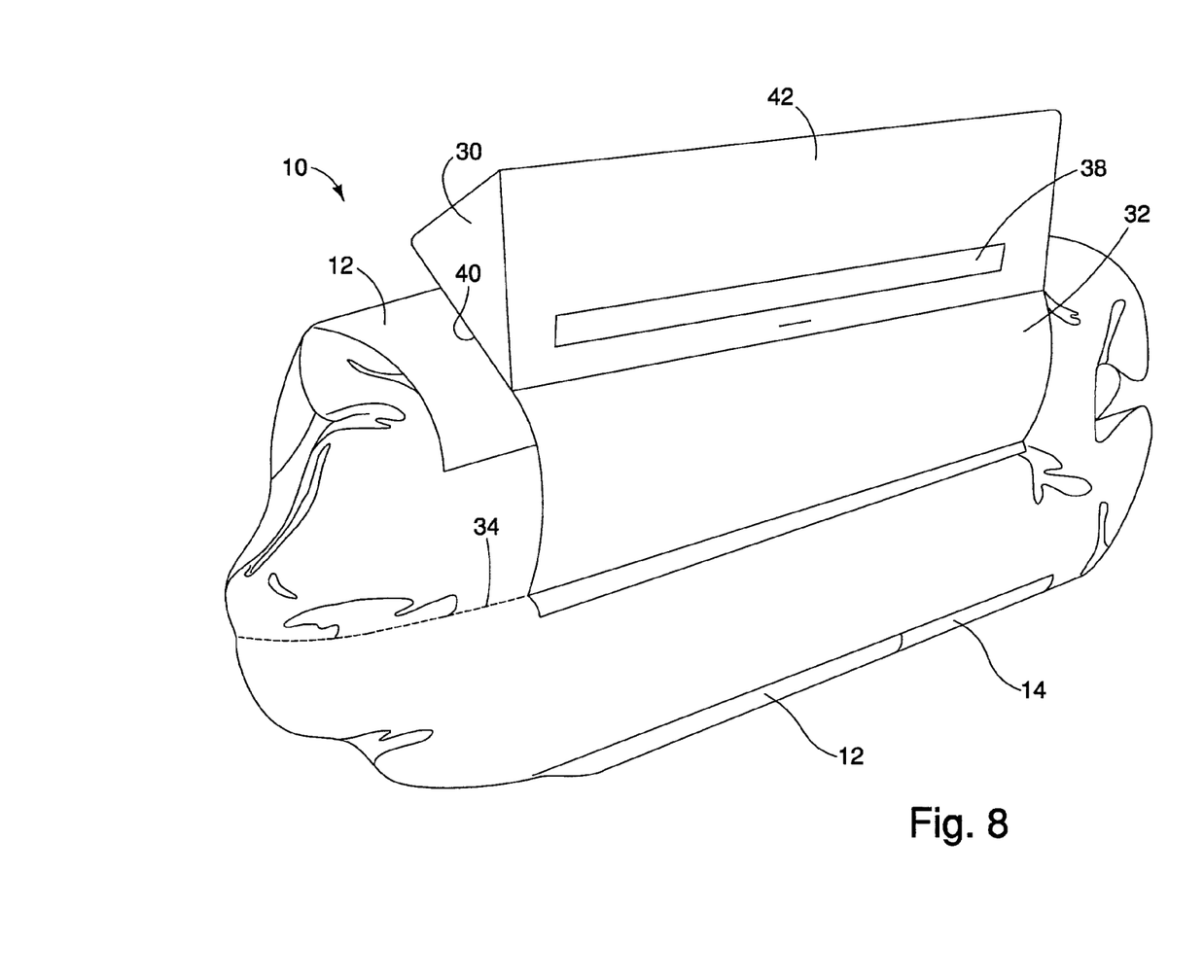
FIG. 8 is a bottom perspective view similar to FIG. 7, showing the stabilization block temporarily affixed to the side of the boot, in the same fashion as illustrated in FIG. 6.

Another embodiment of the invention is shown in FIGS. 6 through 8. Elements of the invention that are the same as described above bear the same reference characters.

In this form of the invention, the wedge 30 is another form of the stabilization block according to the invention and is essentially identical to the wedge 22, except that it is permanently secured to the boot 10. The wedge 30, however, could be another shape. A tether 32 is secured to and extends from the wedge 30 and is secured to and extends from the boot 10. The boot 10 typically has a stitching 34 extending longitudinally, and advantageously, the tether 32 can be stitched to the boot 10 by the stitching 34, as shown, or by separate stitching. However, other means of affixing, such as adhesives, heat staking, sonic welding, riveting, or any other typical means of attaching can be used in appropriate situations, so long as the tether 32 is permanently secured to the boot 10.

The tether 32 preferably comprises an elongated strap, just as the strap 24 of the first form of the invention. While the tether 32 is shown extending the length of the wedge 30, it can be shorter, if desired, while still maintaining a permanent connection to the boot 10.

In this form of the invention, the fastener comprises a first fastener element on the wedge 30 and, similar to the first form of the invention, a second fastener element on the boot 10, that second fastener element comprising the fastener segments 12 and 14. The first fastener element comprises one fastener segment 36 on one face of the wedge 30 and a second fastener segment 38 on a second face of the wedge 30. The fastener segments 36 and 38 complement the fastener segments 12 and 14 in that one of either the segments 12 and 14 or the segments 36 and 38 is preferably a hook element, while the other is a loop element. Thus, when the wedge 30 is applied to the boot 10 as illustrated in the drawing figures, the hook and loop elements engage and hold the wedge 30 in place on either side of the boot 10. For illustration purposes, the fastener segment 36 is shown on a face 40 while the fastener segment 38 is shown on a face 42, although obviously the fastener segments, which are identical, can be reversed.

While it is preferred that the fastener be used, in some instances a fastener may not be necessary. In those instances, the length of the tether 32 will dictate positioning of the wedge 30 for stabilizing the boot 10.

As shown, the tether 32 is secured to the wedge 30 between the faces 40 and 42. Just as in the first form of the invention, the tether 32 is secured in some means forming a permanent connection to the wedge 30.

As shown in the drawing figures, the stitching 34 is midway between the fastener segments 12 and 14 on opposite sides of the boot 10, and therefore the wedge 30 can be easily affixed to either side of the boot 10, depending on where stabilization is required. While it is preferred that the tether is secured at a midpoint between the opposite fastener segments on the boot 10, that is not mandatory and the dimension of the tether 32 extending between the boot 10 and the wedge 30 will determine where the tether 32 can be affixed to the boot 10, with obviously the minimum dimension of the tether 32 being that sufficient to allow the wedge 30 to be affixed to either side of the boot 10.

In accordance with a method according to the invention for stabilizing the boot 10 includes, preferably, the fastener segments 12 and 14 on opposite sides of the boot, and the wedge 30 is tethered to the boot 10 at a fixation location which preferably is the point of the stitching 34. The tether 32 is then of a length sufficient to extend from the fixation location to the fastener segment. For stabilization of the boot, the wedge 30 is pivoted about the tether to engage either of the fastener segments 36 or 38 on its respective side of the boot 10.

Various changes can be made to the invention without departing from the spirit thereof or scope of the following claims.

What is claimed is:

1. A stabilized prevention and therapeutic/treatment boot, comprising:
   a. a boot shaped to engage a foot and lower leg,
   b. a stabilization block, and
   c. a tether secured to and extending from said block and secured to and extending from said boot.

2. The stabilized boot according to claim 1, including a fastener for temporarily affixing said stabilization block in place on said boot.

3. The stabilized boot according to claim 1, in which said stabilization block is elongated and generally triangular in cross-section.

4. The stabilized boot according to claim 1, in which said tether comprises an elongated strap.

5. The stabilized boot according to claim 2, in which said fastener comprises a first fastener element on said stabilization block and a second fastener element on said boot.

6. The stabilized boot according to claim 5, in which said fastener elements comprise hook-and-loop elements.

7. The stabilized boot according to claim 5, in which said first fastener element comprises one fastener segment on one face of said stabilization block and a second fastener segment on a second face of said stabilization block.

8. The stabilized boot according to claim 7, in which said tether is secured to said block between said faces.

9. The stabilized boot according to claim 5, in which said second fastener element comprises one fastener segment on one side of said boot and a second fastener segment on an opposite side of said boot.

10. The stabilized boot according to claim 9, in which said tether is secured to said boot between said fastener segments.

11. A stabilized prevention and therapeutic/treatment boot, comprising
   a. a boot shaped to engage a foot and lower leg,
   b. an elongated, triangular stabilization block,
   c. a tether secured to and extending from said block and secured to and extending from said boot, and
   d. a fastener for temporarily affixing said stabilization block in place in one of two orientations on said boot, said fastener comprising
      i. a first fastener element on said stabilization block, and
      ii. a second fastener element on said boot, wherein
      iii. said first fastener element comprises one fastener segment on one face of said stabilization block and a second fastener segment on a second face of said stabilization block, and
      iv. said second fastener element comprises one fastener segment on one side of said boot and a second fastener segment on an opposite side of said boot.

12. The stabilized boot according to claim 11, in which said fastener elements comprise hook-and-loop elements.

13. The stabilized boot according to claim 11, in which said tether is secured to said block between said faces.

14. The stabilized boot according to claim 11, in which said tether is secured to said boot between said fastener segments.

15. The stabilized boot according to claim 11, in which said tether comprises an elongated strap.

16. A method of stabilizing a prevention and therapeutic/treatment boot, in which the boot includes at least one fastener segment on the boot, the method comprising
   a. tethering a stabilization block to the boot at a fixation location proximate said fastener segment with a strap of a length at least sufficient to extend from said fixation location to said fastener segment, and
   b. pivoting said stabilization block about said strap to engage a fastener segment on said stabilization block with said fastener segment on the boot.

17. The method according to claim 16, in which said boot includes on fastener segment on one side of the boot and a second fastener segment on an opposite side of said boot, and method step "a" includes tethering said stabilization block to said boot at said fixation location, with said fixation location being approximately equidistant between said first and second fastener segments.

* * * * *